United States Patent [19]

May

[11] Patent Number: 4,963,324

[45] Date of Patent: Oct. 16, 1990

[54] COLORIMETRIC DOSIMETER

[75] Inventor: Wolfgang May, Reinfeld, Fed. Rep. of Germany

[73] Assignee: Drägerwerk Aktiengesellschaft, Lübeck, Fed. Rep. of Germany

[21] Appl. No.: 239,319

[22] Filed: Sep. 1, 1988

[30] Foreign Application Priority Data

Sep. 1, 1987 [DE] Fed. Rep. of Germany ....... 8711788

[51] Int. Cl.$^5$ ............................................. G01N 21/78
[52] U.S. Cl. ........................................ 422/60; 422/56;
422/57; 422/58; 422/59; 422/88; 436/167;
436/169; 436/170; 436/902
[58] Field of Search ............... 422/56, 59, 60, 88,
422/58, 57; 436/167, 902, 169, 170

[56] References Cited

U.S. PATENT DOCUMENTS 2,371,405  3/1945  Munn ................................... 422/59
3,620,677 11/1971  Morison .
4,748,930  6/1988  Leichnitz ........................... 436/902
4,844,867  7/1989  Bäther .................................. 422/60

FOREIGN PATENT DOCUMENTS 92101 10/1983 European Pat. Off. ............ 436/902

Primary Examiner—Robert J. Hill, Jr.
Assistant Examiner—Abanti B. Singla
Attorney, Agent, or Firm—Walter Ottesen

[57] ABSTRACT

The invention relates to a colorimetric dosimeter including an indicator housing openable at one end and having a wall defining an interior space extending along the length thereof. The housing is partitioned into a first portion starting at the one end and a second portion following behind the first portion. A strip indicator defines a high-sensitivity region and is disposed in the first portion so as to conjointly define a clear through diffusion passage with the wall which extends to the second portion. A granular indicator defining a low-sensitivity region is disposed in the second portion.

5 Claims, 1 Drawing Sheet

COLORIMETRIC DOSIMETER

FIELD OF THE INVENTION

The invention relates to a colorimetric dosimeter having an indicator displaying a linear coloration. The indicator is subdivided into regions having different indicating sensitivities.

BACKGROUND OF THE INVENTION

A dosimeter of this kind is disclosed in U.S. Pat. No. 3,620,677. This dosimeter includes a housing which closely encloses a strip-like wick and is in contact engagement therewith. The wick can take on different geometric forms. The specimen to be investigated diffuses along the wick and brings about a coloration as a consequence of a chemical reaction with an indicator substance provided on the wick. Either more or less quantities of an indicator substance are provided in dependence upon the contour of the strip-like duct whereby the detection sensitivity for larger or smaller quantities of contaminants is determined.

Since the strip-like indicator strip of the known dosimeter completely fills out the indicator housing, a diffusion of gaseous material to be detected is greatly restricted and requires a correspondingly long diffusion time. In particular, these diffusion times become impermissibly long if the smallest quantities of gaseous contaminants are to be detected.

SUMMARY OF THE INVENTION

It is an object of the invention to improve upon a colorimetric dosimeter of the kind described above in order to make possible a dosimetric measurement of the smallest quantity of gaseous contaminants in several sensitivity stages with the indicator carrier being suitable for a highly sensitive measurement. It is a further object of the invention to provide such a colorimetric dosimeter wherein the diffusion path for larger quantities of gaseous contaminants is not restricted thereby.

According to a feature of the colorimetric dosimeter of the invention, a high-sensitivity region having a strip indicator and a low-sensitivity region having a granular indicator are provided. The strip indicator provides a clear diffusion path between the strip indicator and the indicator housing.

The contaminants to be detected can diffuse unimpeded along the strip indicator and are collected by the latter for detecting the smallest quantities of contaminants in order to form a corresponding coloration zone thereon. Greater quantities of contaminant which have completely exhausted the strip indicator can penetrate farther to the granular indicator and be absorbed by the latter in larger quantities and be displayed by means of a coloration zone. With a housing openable at only one end, the high-sensitivity region can start at the one end and be located directly ahead of the low-sensitivity region having the granular indicator. In this way, an advantageous multilayer dosimeter is obtained in a single housing which can be utilized for dosimetric measurements of different sensitivity stages.

A reagent suitable for detecting a contaminant such as ammonia is mercury (I) nitrate and to detect chlorine, o-tolidine can be utilized as a reagent.

The strip indicator can be defined by a reagent deposited on the inner wall surface of the dosimeter tube to detect the smallest quantities of the contaminant; whereas, the granular indicator for detecting greater quantities of the contaminant can be in the form of a silica gel which is impregnated with the reagent.

According to a further embodiment of the invention, a permeable intermediate layer can be provided between the regions which on the one hand serves to hold the strip indicator and granular indicator in a vibration secure manner while also serving as a diffusion layer for the contaminant to be detected.

Furthermore, it is possible to provide the indicator housing with two openable ends which open to the strip indicator and the granular indicator, respectively, with both regions being separated from each other by means of an impermeable intermediate layer. Depending upon the quantity of contaminant present, this affords the advantage that only the region with the strip indicator need be opened for measuring very low quantities and only the region of the granular indicator need be opened to measure higher quantities of contaminant. The two regions can be provided with respective indicators having different sensitivities for different gaseous contaminants whereby a double dosimeter is obtained which provides detection of various gases in different quantities.

It is especially desirable to configure the inner wall of a tubular indicator as a high-sensitivity region. In this way, an especially favorable relationship between the volume of the diffusion length and of the indicator surface is obtained.

In an advantageous manner, the low-sensitivity region can be formed by means of a bed of the granular indicator in the indicator housing.

With the dosimeter according to the invention, all gases can be detected which lead to a coloration of a reagent.

Generally, it should be noted that it is advantageous to provide a sensitive layer as well as an insensitive layer in a dosimeter when a concentration of a contaminant is not known, for example, during a work day at a work location or at a technical facility. In this instance, the sensitive part can detect the smallest quantities of contaminant. On the other hand, if during the monitoring time an unexpected and unobservable higher quantity of contaminant should appear, then the sensitive detecting portion would be colored along its entire length. If no additional insensitive detecting part were present for higher quantities of the contaminant, then one would not know in which quantity the contaminant had occurred, for example, from an accidental eruption. By providing the additional insensitive detection portion, one would know and be able to monitor the high quantity of the contaminant.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
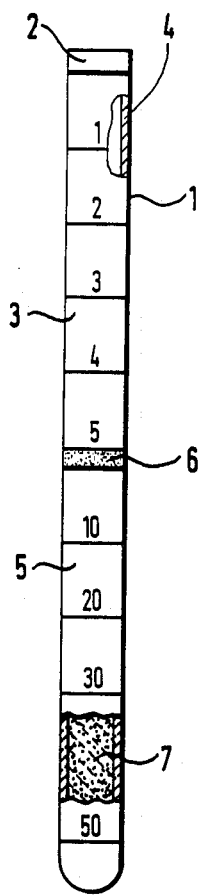
FIG. 1 is a side elevation view of a tubular dosimeter of the invention with one openable end; and, FIG. 2 is another embodiment of the dosimeter according to the invention having two openable ends.

FIG. 1 shows a dosimeter in the form of a tubular indicator housing made of glass which has only one openable end 2 for the ingress of the contaminant to be detected. A high-sensitivity region 3 starts at the openable end 2 and has a reagent in the form of a strip-like indicator 4 which is deposited on the inner wall of the indicator housing 1. The region 3 is provided with an appropriate scale of 1 to 5 for reading off the coloration zone which forms on the inner wall. The scale has the dimensions of ppm x h. A low-sensitivity region 5 extends from the high-sensitivity region 3 and is closed off by a permeable intermediate layer 6 for holding a granular indicator 7 which can be a silica gel impregnated with the reagent. The outer surface of the indicator housing 1 is provided with an appropriate scale (ppm×h) in the region 5 of the granular indicator. The scale has values which extend from 10 to 50.

For detecting ammonia, for example, mercury (I) nitrate is used as the reagent; and, to detect chlorine, o-tolidine can be utilized as a reagent. Thus, for detecting ammonia, mercury (I) nitrate would be deposited on the inner wall surface of region 3 and this same reagent would be impregnated into the silica gel.

Figure 2:
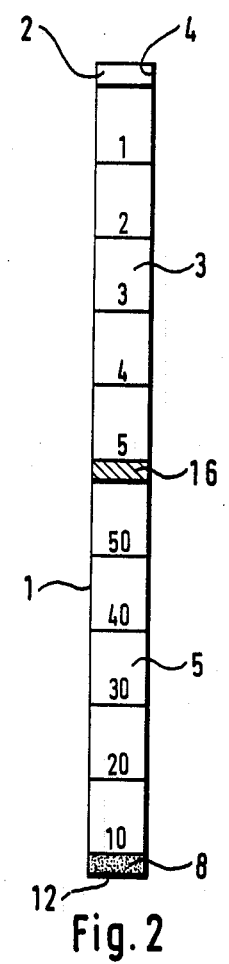

In FIG. 2, the indicator housing 1 is provided with two openable ends (2, 12) and the high-sensitivity region 3 which includes strip-like indicator 4 is separated from the low-sensitivity region 5 by an impermeable intermediate layer 16. A diffusion raster 8 is provided at the corresponding openable end 12 for fixing the granular indicator. The diffusion raster 8 can be in the form of a porous plug made as a woven fabric of steel.

The scales of the respective regions (3 and 5) is applied to the outer surface of the indicator housing 1 and start from corresponding ones of the openable ends (2 and 12).

The openable end 2 of the detector housing of FIG. 1 and the openable ends (2, 12) of the detector housing of FIG. 2 can be provided with a scoring to facilitate snapping off of the ends prior to use. The scoring can be provided, for example, as shown in FIG. 1 of copending application Ser. No. 824,191, filed on Jan. 30, 1986, and incorporated herein by reference.

It is understood that the foregoing description is that of the preferred embodiments of the invention and that various changes and modifications may be made thereto without departing from the spirit and scope of the invention as defined in the appended claims.

What is claimed is:

1. A colorimetric dosimeter comprising:
   an elongated indicator housing openable at one end and having an inner wall surface defining an interior space extending along the length thereof;
   said housing being partitioned into a first portion starting at said one end and a second portion following behind said first portion;
   a strip indicator defining a high-sensitivity region and being disposed in said first portion so as to conjointly define a clear through diffusion passage with said inner wall surface in said first portion which extends to said second portion; and,
   a granular indicator defining a low-sensitivity region and being disposed in said second portion.

2. The colorimetric dosimeter of claim 1, further comprising a permeable intermediate layer disposed in said housing between said first portion and said second portion for partitioning said high-sensitivity region from said low-sensitivity region.

3. The colorimetric dosimeter of claim 1, further comprising an impermeable intermediate layer disposed in said housing between said first portion and said second portion for partitioning said high-sensitivity region from said low-sensitivity region.

4. The colorimetric dosimeter of claim 1, wherein said housing is a tubular housing and said strip indicator is formed on a portion of said inner wall surface in said first portion.

5. The colorimetric dosimeter of claim 1, wherein said granular indicator is a granular bed filling said housing in said second portion thereof.

* * * * *